United States Patent
Chou et al.

(10) Patent No.: US 7,374,770 B2
(45) Date of Patent: May 20, 2008

(54) TOPICAL COMPOSITION FOR FOLLICULAR DELIVERY OF AN ORNITHINE DECARBOXYLASE INHIBITOR

(75) Inventors: Joyce T. Chou, Fremont, CA (US); Prakash Parab, Monroe Township, NJ (US)

(73) Assignee: SkinMedica, Inc., Carlsbad, CA (US)

( * ) Notice: Subject to any disclaimer, the term of this patent is extended or adjusted under 35 U.S.C. 154(b) by 691 days.

(21) Appl. No.: 10/219,087

(22) Filed: Aug. 13, 2002

(65) Prior Publication Data

US 2003/0053973 A1 Mar. 20, 2003

Related U.S. Application Data

(60) Provisional application No. 60/312,657, filed on Aug. 15, 2001.

(51) Int. Cl.
*A61K 8/00* (2006.01)
*A61K 31/197* (2006.01)

(52) U.S. Cl. .................. 424/401; 424/484; 424/69; 514/564; 514/673; 514/944; 514/945; 514/937; 514/946; 514/947; 514/969

(58) Field of Classification Search .................. 424/401; 514/561, 553
See application file for complete search history.

(56) References Cited

U.S. PATENT DOCUMENTS

| | | | |
|---|---|---|---|
| 3,925,012 A * | 12/1975 | Ringel et al. ................ | 8/602 |
| 4,201,788 A | 5/1980 | Voorhees et al. | |
| 4,413,141 A | 11/1983 | Bey et al. | |
| 4,421,768 A | 12/1983 | Casara et al. | |
| 4,496,588 A | 1/1985 | Bey et al. | |
| 4,720,489 A | 1/1988 | Shander | |
| 5,095,007 A | 3/1992 | Ahluwalia | |
| 5,096,911 A | 3/1992 | Ahluwalia et al. | |
| 5,132,293 A | 7/1992 | Shander et al. | |
| 5,217,886 A | 6/1993 | Au et al. | |
| 5,648,394 A * | 7/1997 | Boxall et al. ................ | 514/567 |
| 5,851,537 A | 12/1998 | Alberts et al. | |
| 5,945,409 A * | 8/1999 | Crandall ...................... | 514/78 |
| 2003/0035818 A1 | 2/2003 | Styczynski et al. | |
| 2003/0036561 A1* | 2/2003 | Styczynski et al. ......... | 514/564 |

FOREIGN PATENT DOCUMENTS

| | | |
|---|---|---|
| CA | 2455036 | 2/2003 |
| EP | 0439335 | 7/1991 |

(Continued)

OTHER PUBLICATIONS

Physicians' Desk Reference, 55 Edition, pp. 1031-1033, (2001).

*Primary Examiner*—Neil S. Levy
(74) *Attorney, Agent, or Firm*—Wilson Sonsini Goodrich & Rosati

(57) ABSTRACT

Polyethylene glycol ethers of alkyl alcohols having the general formula $CH_3(CH_2)_xCH_2(OCH_2CH_2)_nOH$ wherein x is 8 to 20 (of which ceteareth-20, steareth-20 and steareth-100 are preferred), poloxamer 185, poloxamer 407, N,N-dimethyl dodecylamine N-oxide, and mixtures thereof, are employed to increase follicular delivery and/or follicular residence time of certain water soluble ornithine decarboxylase inhibitors of which 2(difluoromethyl)-2,5-diamino pentanoic acid and its pharmaceutically acceptable salts, hydrates, optical enantiomers and racemic mixture are preferred.

26 Claims, 3 Drawing Sheets

Follicular enhancement ratio of eflornithine from various formulations in comparison to Vaniqa®

FOREIGN PATENT DOCUMENTS

| | | |
|---|---|---|
| JP | H01-258616 | 10/1989 |
| JP | H04-095019 | 3/1992 |
| JP | H04-210907 | 8/1992 |
| JP | H05-170624 | 7/1993 |
| JP | H06-500335 | 6/1994 |
| JP | H08-507785 | 8/1996 |
| JP | H11-267105 | 10/1999 |
| WO | WO-92-03140 A1 | 3/1992 |
| WO | WO 94-21217 A1 | 9/1994 |
| WO | WO 98/25603 | 6/1998 |
| WO | WO 03/013469 | 2/2003 |
| WO | WO 03/013469 A1 | 2/2003 |

* cited by examiner

Follicular enhancement ratio of eflornithine from Lotion A in comparison to Vaniqa®

Follicular enhancement ratio of eflornithine from various formulations in comparison to Vaniqa®

Follicular enhancement ratio of eflornithine from various formulations in comparison to Vaniqa®

TOPICAL COMPOSITION FOR FOLLICULAR DELIVERY OF AN ORNITHINE DECARBOXYLASE INHIBITOR

RELATED APPLICATIONS

This application claims priority to Provisional Application No. 60/312,657 entitled TOPICAL COMPOSITION FOR FOLLICULAR DELIVERY OF AN ORNITHINE DECARBOXYLASE INHIBITOR filed on Aug. 15, 2001. The subject matter of the aforementioned application is hereby incorporated by reference in its entirety.

FIELD OF THE INVENTION

The present invention relates to a topical formulation that enhances the delivery, and preferably increases the retention time, of an ornithine decarboxylase inhibitor (hereinafter referred to as an "ODC inhibitor") in the hair follicles of mammalian skin, preferably human skin, to regulate, preferably decrease, the rate of hair growth. The preferred ODC inhibitor is 2-(difluoromethyl)-2,5-diaminopentanoic acid, which is also identified as alpha-(difluoromethyl) ornithine (hereinafter referred to as "DFMO"). DFMO hydrochloride is most preferred and is henceforth referred to herein by its USAN name "Eflornithine." Eflornithine is a highly charged compound that does not readily penetrate the skin or hair follicles. The composition of the present invention comprises an ODC inhibitor, preferably DFMO, its pharmaceutically acceptable salts and hydrates, optical enantiomers (R,S) and racemic mixtures (RS), more preferably Eflornithine and certain pharmaceutical solubilizers found by the present inventors to enhance the delivery of the ODC inhibitor into hair follicles, as judged by an in vitro cadaver skin model disclosed herein.

BACKGROUND OF THE INVENTION

ODC inhibitors, particularly, DFMO and its pharmaceutically acceptable salts and hydrates, are known to be topically useful in regulating hair growth in mammals, particularly humans (see U.S. Pat. No. 4,720,489 and P.D.R., 55 Edition, 2001, pages 1031-1033).

PCT WO 98/25603 discloses an isomeric pharmaceutical formulation containing DFMO. Examples 7 and 8 respectively teach preparation of a [−]-DFMO containing lotion and topical solution. Patentees teach that the lotion formulation is useful for the treatment or prevention of skin melanoma. The solution is disclosed to be suitable for topical treatment or prevention of proliferative skin disorders. The treatment of such conditions does not require delivery of drug to the hair follicles. More importantly, there is no appreciation whatsoever of enhancement of delivery of DFMO to the skin, much less to the hair follicle. Although Example 7 employs Poloxamer 235, there is no disclosure whatsoever of any advantage for it other than its known use as a co-emulsifier.

U.S. Pat. No. 5,851,537 discloses the topical application of alpha-DFMO monochloride monohydrate for preventing skin cancer. The drug, carried in a hydrophilic cream base, is applied to actinic keratoses. Hydrophilic cream contains 0.025% methyl paraben, 0.015% propyl paraben, 1% sodium lauryl sulfate, 12% propylene glycol, 25% stearyl alcohol, 25% petrolatum and 37% water. There is no disclosure whatsoever of a follicular delivery enhancing component or the desirability of including it. In point of fact, patentees state that the compositions of their invention contain no absorption enhancer.

U.S. Pat. No. 4,720,489 discloses a process for reducing the rate and altering the character of human hair growth. The process comprises applying to the skin a composition containing an ODC inhibitor. Patentees, however, fail to disclose or even appreciate the desirability of targeting the ODC inhibitor to the hair follicle or the need to use a follicular delivery enhancer for such purpose.

U.S. Pat. No. 5,648,394 discloses a topical composition for inhibiting mammalian hair growth. The composition comprises about 1 to 20 parts by weight of a water-soluble, hair-growth-inhibiting drug dispersed in about 99 to 80 parts by weight of an oil-in-water emulsion based vehicle. In parts by weight, the vehicle is comprised of water 78 to 87; glyceryl stearate 2.8 to 4.8; PEG-100 stearate 2.7 to 4.7; cetearyl alcohol 1.9 to 3.3; ceteareth-20 1.6 to 2.7; mineral oil 1.7 to 2.7; stearyl alcohol 1.0 to 2.0; and dimethicone 0.3 to 1.0. Patentees contend that compositions of the invention are superior in efficacy to a water-ethanol composition containing penetration enhancers. They state that this suggests that the compositions of the invention achieve either enhanced skin penetration of the active or increased residence time of the active at the treated site. Patentees, however, fail to teach or even suggest which composition ingredient, or combination of ingredients, accounts for the enhanced skin penetration or increased residence time. Thus, one skilled in the art would attribute it to the entire composition as opposed to any particular composition component or combination of components.

Patentees prepared the vehicles of Examples I and II (see Col. 2 of U.S. Pat. No. 5,648,394). Test compositions containing 2.5, 5, 10, and 15 percent DFMO were then prepared using the two vehicles. A composition containing 10 percent DFMO in water-ethanol was also prepared. The compositions were then tested for hair growth inhibition using the hamster flank model (see Example, Col. 3 of U.S. Pat. No. 5,648,394). The test results (set forth in the table in Column 3 of U.S. Pat. No. 5,648,394) demonstrate that, in each case, the DFMO composition prepared using the vehicle of Example II had a higher percentage of inhibition than the respective DFMO composition prepared using the vehicle of Example I. Consequently, even if one skilled in the art were to select, for example, ceteareth-20, out of the ten ingredients that make up the vehicle, he or she would be led away from the present invention. Although the vehicle of Example II contained less ceteareth-20 than the vehicle of Example I, patentees test results show that the percentage of inhibition obtained with the use of the vehicle of Example II was higher. Thus, if one skilled in the art wishing to increase the percentage of inhibition is led to ceteareth-20, he or she would be led by the teaching of this patent to reduce the amount of ceteareth-20 contained in the composition. The skilled artisan would not increase the amount of ceteareth-20 or, for that matter, the amount of any other ingredient(s) of the vehicle.

The prior art, typified by U.S. Pat. No. 5,648,394, demonstrates the effectiveness of ODC inhibitors for inhibiting hair growth by measuring changes in flank organ hair mass in adult male hamsters treated with ethanol solutions of the ODC inhibitors. The standard hamster flank organ mass study is described in, for example, U.S. Pat. Nos. 4,720,489, 5,095,007, 5,096,911 and 5,132,293.

Prior art topical DFMO compositions generally show relatively low efficacy in humans. Possibly the presumed levels of DFMO achievable in human follicles through use of prior art topical DFMO compositions are insufficient to cause sustained and effective inhibition of target enzyme ornithine decarboxylase ("ODC").

Complicating matters is the fact that with hair mass analysis, it is very difficult to differentiate the efficacy of different DFMO formulations. This is in part due to physical effects of lotion-based formulations on hamster hair.

The present inventors hypothesized that hair follicle atrophy could represent a surrogate end point for DFMO efficacy.

Clinical studies that were later carried out confirmed that hair follicle atrophy is indeed a valid marker for DFMO efficacy.

The half-life of ODC in the hair follicle is about thirty minutes. In order to block ODC enzyme when it is present in the hair follicle, the ODC inhibitor must be present in the follicle in sufficient amount and for a prolonged duration.

Thus, an aim of the present invention was to identify excipients that would target a high concentration of an ODC inhibitor, preferably DFMO and its pharmaceutically acceptable salts, hydrates, optical enantiomers and racemic mixtures, more preferably Eflornithine, to the hair follicle and, ideally, keep it there for a prolonged duration.

In order to determine differences in the efficacy of DFMO in lotion-based formulations, as well as the onset of action of DFMO, independent of hair growth, the present inventors had to develop a method of analysis of human hair follicle bulbs.

Another goal of the present invention was to develop a formulation that would enhance the delivery of an ODC inhibitor, particularly DFMO and its pharmaceutically acceptable salts, hydrates, optical enantiomers and racemic mixture, to the pilosebaceous unit target site (consisting of the hair follicle, hair shaft and sebaceous gland) and maintain its concentration over a prolonged period of time. Since ornithine decarboxylase has a fifteen-minute to one-hour half-life it is highly desirable that the ODC inhibitor be present in the hair follicle for as long a time as is possible.

SUMMARY OF THE INVENTION

The present invention is based on the surprising finding that of the many penetration enhancers known to the dermatological prior art, only a very select few were found by the present inventors to be effective in enhancing follicular penetration of ODC inhibitors, such as DFMO and its pharmaceutically acceptable salts and hydrates, optical enantiomers and racemic mixtures, particularly Eflornithine.

As noted earlier, the present inventors were required to develop an in vitro cadaver scalp/beard skin model to assess the degree of enhancement provided to the follicular take-up of the ornithine carboxylase inhibitor.

DETAILED DESCRIPTION OF THE INVENTION

The present invention will now be described in greater detail and with reference to the examples and drawings in which:

FIG. 1 is a graph of the follicular enhancement ratio of Eflornithine from steareth-20/steareth 100 Lotion A to the commercially available Vaniqa® Cream formulation (containing 13.9% Eflornithine), at 3 and 24 hours, in cadaver beard skin (5 donors, n=2) employing the hair plucking technique;

FIG. 2 is a graph comparing, at 3 hours, the follicular enhancement ratio of Eflornithine from steareth-20/steareth-100 Lotion A, steareth-20/steareth-100 Lotion B, and poloxamer 185 lotion to the commercially available Vaniqa® Cream formulation (containing 13.9% Eflornithine), in cadaver scalp skin (1 donor, n=4) employing the hair plucking technique; and FIG. 3 is graph comparing, at 3 hours, the follicular enhancement ratios of Eflornithine from aqueous solutions of, respectively, poloxamer 407, steareth-20/steareth-100, poloxamer 185 and lauryl dimethylamine oxide (hereinafter referred to as "LDAO"), to the commercially available Vaniqa® Cream formulation (containing 13.9% Eflornithine), in cadaver scalp skin (1 donor, n=4) employing the hair plucking technique.

In its simplest form the topical compositions of the present invention comprise a water soluble, preferably highly water soluble, ODC inhibitor, an amount of an enhancing agent that enhances the follicular delivery and/or increases the residence time of the ODC inhibitor in the hair follicle, and a pharmaceutically acceptable aqueous vehicle for the enhancing agent and ODC inhibitor.

Water-soluble ODC inhibitors that can be employed in the composition of the present invention are those described in U.S. Pat. Nos. 4,201,788, 4,413,141, 4,421,768 and 4,720,489.

In choosing ODC inhibitors for use in the practice of the instant invention those known to have undesirable secondary pharmacological effects should be avoided. For example, 5-hexyne-1,4-diamine is known to cause increases in brain 4-aminobutyric acid levels.

Preferably, the water-soluble ODC inhibitor is selected from the group consisting of 2-(difluoromethyl)-2,5-diaminopentanoic acid, alpha-ethynyl ornithine, 6-heptyne-2,5-diamine, 2-methyl-6-heptyne-2,5-diamine and pharmaceutically acceptable salts, hydrates and optical enantiomers and racemic mixtures (R, S and RS) thereof. 2-(Difluoromethyl)-2,5-diaminopentanoic acid, its pharmaceutically acceptable salts, hydrates, its (R) and (S) enantiomers and racemic mixture (RS) is more preferred. Eflornithine is most preferred.

The ODC inhibitor, pharmaceutically acceptable salt, hydrate or optical enantiomer or racemate thereof is preferably present in the composition in an amount that is effective to produce a hair growth inhibiting effect on the hair follicle in which case the follicular delivery enhancing agent serves to increase such delivery and/or increase the retention time of the ODC inhibitor in the follicle so that the efficacy of the ODC inhibitor is increased.

Alternatively, the ODC inhibitor, pharmaceutically acceptable salt, hydrate or optical enantiomer or racemate thereof can be present in the composition in an amount that would be insufficient to produce a hair growth inhibiting effect (a sub-therapeutic level) on the hair follicle in the absence of the follicular delivery enhancing agent and the follicular delivery enhancing agent is present in the composition in an amount that enhances the follicular delivery of the ODC inhibitor and/or increases its residence time in the hair follicle so that the ODC inhibitor exerts a therapeutic effect.

The follicular delivery enhancer is present in the composition in an amount sufficient to enhance the follicular delivery of the ODC inhibitor to the hair follicle and/or increase its residence time in the hair follicle. Such amount is readily determinable by one skilled in the art by use of the cadaver skin model disclosed later on herein. Generally, it is present in an amount from about 1.0% to about 25%; preferably from about 2.5% to about 20%; more preferably from about 4% to about 15%; and most preferably from about 5% to about 10%. Moreover, when the enhancer is ceteareth-20, it is preferably present in an amount of at least 3%, more preferably at least 4%. It should be noted that unless indicated to the contrary all percentages are percent w/w based on the total weight of the composition.

To minimize the risk of alteration of other bodily functions through systemic action it is preferred to apply the ODC inhibitors in compositions such that the level of application of the ODC inhibitor will range from about 1 to about 2000 micrograms of active material per square centimeter of skin. Still more preferred is the application of about 50 to about 500 micrograms per square centimeter of skin.

The follicular delivery-enhancing agent of the present invention is selected from the group consisting of:

a. Polyethylene glycol ethers of alkyl alcohols having the general formula $CH_3(CH_2)_xCH_2(OCH_2CH_2)_nOH$ wherein x is 8 to 20, preferably 10 to 16, more preferably 10, 14 or 16, and n is 2 to 100, preferably 2 to 150, more preferably 4 to 100;

the most preferred polyethylene glycol ethers of alkyl alcohols of the above formula being:

steareth-20, a polyethylene glycol ether of stearyl alcohol that has the formula $CH_3(CH_2)_{16}CH_2(OCH_2CH_2)_nOH$ wherein n=20, and is available commercially as Brij® 78, Alkasurf SA®-20, Brox® S-20, Hodag® Nonionic S-20, Lanycol®-78, Lipocol® S-20, Procol® SA-20, Simulsol® 78, Unicol® SA-20, and Volpo® S-20;

steareth-100, a polyethylene glycol ether of stearyl alcohol that has the formula $CH_3(CH_2)_{16}CH_2(OCH_2CH_2)_nOH$ wherein n=100, and is available commercially as Brij® 700, Lanycol®-700, and Volpo® S-100; and ceteareth-20, a polyethylene glycol ether of ceteary1 alcohol having the formula $R(OCH_2CH_2)_nOH$ wherein R represents alkyl groups derived from cetyl and stearyl alcohols and n=20, and available commercially as Brij® 68, Acconon® W 230, Alkasurf® CA-20, Empilan® KM20, Eumulgin® B-2, Hetoxol® CS-20, Hodag® Nonionc CS-20, Incropol® CS-20, Lipocol® SC-0, Macol® CSA-20, Procol® CS-20, Siponic® E-10, Unicol® CSA-20, and Unimul® B-2;

b. Poloxamer 185, copolymers of ethylene oxide and propylene oxide having the formula $HO(C_2H_4O)_a(C_3H_6O)_b(C_2H_4O)_aH$ where a=19 and b=30, and available commercially as Hodag® Nonionic 1065-P, and Pluracare®/Pluronic® P-65;

c. Poloxamer 407 copolymers of ethylene oxide and propylene oxide having the formula $HO(C_2H_4O)_a(C_3H_6O)_b(C_2H_4O)_aH$ where a=98 and b=67, and available commercially as Hodag® Nonionic 1127-F, Macol® 27, Pluracare®/Pluronic® F-127, and Synperonic® PE/F127;

d. N,N-dimethyl dodecylamine N-oxide ("LDAO");

e. and mixtures thereof.

The composition of the present invention can also include an inhibitor of S-adenosylmethionine decarboxylase in an amount effective to reduce the rate and alter the character of mammalian hair growth. The S-adenosylmethionine decarboxylase inhibitor is preferably selected from the group consisting of methylglyoxal bis (guanylhydrazone), diethylglyoxal bis (guanylhydrazone), and 5'-deoxy-5'-{N-methyl-N-} aminodenosine.

The amount of inhibitor of S-adenosylmethionine decarboxylase present in the composition should be such that on application from 1 to 5000 micrograms of S-adenosylmethionine decarboxylase active is delivered per square centimeter of skin.

Solution and oil-in-water emulsions are the preferred forms of the composition of the instant invention. However, other forms can be employed. For example, gels, creams, ointments, sticks, pastes, shampoos, foams, patches, mousses, and the like.

Although other ingredients generally incorporated in oil-in-water emulsion based topical lotions and topical aqueous solutions will readily suggest themselves to one skilled in formulating such compositions, the effect of each such ingredient must be considered. The addition of an ingredient in which the ODC inhibitor is highly soluble can negatively impact follicular delivery. For example, when LDAO is employed in the composition of the invention, glycerin should be avoided or, when used, should be restricted in amount so that it does not adversely impact follicular delivery.

Although Eflornithine was employed in the examples that follow, it should be noted that any suitable ODC inhibitor could be employed, for example, alpha-ethynyl ornithine; 6-heptyne-2,5-diamine or 2-methyl-6-heptyne-2,5-diamine. Eflornithine was employed, as it is most preferred.

The test procedure is set forth in Example 1 below.

It should be noted that the examples as set forth herein are meant to exemplify the various aspects of carrying out the invention and are not intended to limit the invention in any way.

It should be further noted that in the Examples reference to Vaniqa® is to Westwood-Squibb Colton Holdings Partnership's commercially available cream formulation containing 13.9% Eflornithine hydrochloride.

EXAMPLE 1

Methods to Measure Delivery of Drug to the Hair Follicles

Harvest cadaver scalp or beard skin with hair within 24 hours post-mortem. Keep the harvested skin at −70° C. Before use, thaw the frozen skin in normal saline maintained at 30° C. After thawing, trim off the excessive subcutaneous fat from the skin and trim the hair with an electric clipper so that the hair length on the skin surface is from 1 to 2 mm. Then, cut the skin into appropriate size pieces and mount them on Franz diffusion cells (0.63 cm$^2$) containing Sorensen buffer (pH 7.4), maintained at 37° C., as receptor phase. Using a glass rod, gently apply 30 μl radiolabeled formulation (1-3 μCi of radiolabeled Eflornithine at a minimum radiochemical purity of 99%) to the skin surface. After formulation application, conduct in vitro diffusion study for 3 to 24 hours, Vaniqa® is included in every study as a positive control. The amount of drug delivered to the hair follicles is measured by either a hair plucking technique or a microsurgical technique. The two techniques are described below:

Hair Plucking Technique

At the end of the diffusion study, rinse the skin, with the donor chamber intact, five (5) times with 0.6 ml of purified water. After each rinse, swab the skin gently with a clean Q-tip to remove the liquid rinse using a disposable pipette. After rinsing and swabbing, dismantle the diffusion chamber. Then, wipe off excess formulation and water on the skin surface with a clean Q-tip. Remove the skin and place skin epidermis side up on a board lined with a piece of Parafilm®. Tape strip the skin six (6) times to remove residual formulation on the skin surface. After skin stripping, pluck the hair from the skin area exposed to formulation treatment using a pair of clean disposable tweezers. The hair plucking technique is as followed:

Mark the treated skin area (skin surface) with an 8 mm biopsy punch by pressing it gently against the skin to make an indentation.

Remove hair from the marked skin area by plucking with a pair of clean disposable tweezers.

Collect the plucked hair follicles on a piece of tape, collect 20 hair follicles per treated area.

Place hair follicles in Solvable® to solubilize hair and analyze drug content by radiochemical assay.

Microsurgical Technique

At the end of the diffusion study, carefully rinse the skin, with donor chamber intact, five (5) times with 0.6 ml of water. After each rinse, swab the skin gently with a clean Q-tip and remove the rinse using a disposable plastic pipette. Following rinsing and swabbing, dismantle the chamber and very gently wipe off excess formulation on the skin with the aid of a clean Q-tip. Remove the skin and place it (with the epidermis side up) on a board lined with Parafilm® (use a pair of clean disposable plastic tweezers to handle the skin). Then, use an 8 mm dermal punch to core the center of the treated site, coring from the dermis to the epidermis. After the 8 mm core is obtained, the subcutaneous tissue is viewed under the stereomicroscope to locate hair bulbs. In the anagen phase, hair follicle bulbs extend deep into the subcutaneous tissue in a manner that makes the terminal portion. Twenty bulbs from each treated skin area are cut off with a pair of microscissors. The bulbs are collected on a piece of filtered paper and solubilized in 1 ml of Solvable®. A radiochemical assay is carried out on the dissolved hair bulb to measure the amount of drug delivered to the target area. Using the procedure of Example 1, the follicular enhancement ratio of Eflornithine HCl was determined for the following compositions.

It should be noted that unless indicated to the contrary all percentages are percent weight/weight based on total weight of the composition.

It should also be noted that "Follicular Enhancement Ratio," as used herein, means the ratio of the geometric mean of the amount of Eflornithine delivered to the hair follicles from the test formulation to the geometric mean of the amount of Eflornithine delivered to the hair follicles from Vaniqa® Cream.

EXAMPLE 2

Lotion A

| Component | % |
|---|---|
| Steareth-20 | 5 |
| Steareth-100 | 5 |
| Mineral oil | 1.9 |
| Stearyl alcohol | 3 |
| Dimethicone-200 | 1 |
| Cetyl alcohol | 1 |
| Eflornithine monohydrate* | 15 |
| Water | 68.1 |

*Equivalent to 13.9% Eflornithine

The above lotion composition was prepared as follows:

The aqueous phase, consisting of the Eflornithine monohydrate and water, was heated to a temperature of 65 to 70 degrees C. The oil phase, consisting of the remaining ingredients, was heated to temperature of 65 to 70 degrees C. The oil and water phases were then combined under agitation and mixing was continued until the temperature reached 30 to 35 degrees C.

EXAMPLE 3

Lotion B

| Component | % |
|---|---|
| Steareth-20 | 5 |
| Steareth-100 | 5 |
| Mineral oil | 1.9 |
| Stearyl alcohol | 3 |
| Dimethicone-200 | 0.5 |
| Glyceryl stearate & PEG-100 stearate | 2.5 |
| Cetearyl alcohol & Ceteareth-20 | 2.5 |
| Eflornithine monohydrate* | 15 |
| Water | 64.6 |

*Equivalent to 13.9% Eflornithine

The above lotion composition was prepared in accordance with the method of Example 2.

EXAMPLE 4

Poloxamer 185 Lotion

| Component | % |
|---|---|
| Glyceryl stearate and PEG-100 stearate | 2.5 |
| Mineral oil | 2 |
| Stearyl alcohol | 2 |
| Dimethicone-200 | 0.5 |
| Steareth-2 | 0.75 |
| Cetyl alcohol | 1 |
| Poloxamer 185 | 10 |
| Eflornithine monohydrate* | 15 |
| Water | 66.25 |

*Equivalent to 13.9% Eflornithine

The above composition was prepared in accordance with the method of Example 2 with the poloxamer 185 being incorporated in the aqueous phase.

As is shown in Examples 2 through 4 above, the composition of the present invention can be in the form of a lotion, more particularly, an oil-in-water emulsion. However, as is exemplified by Examples 5 through 8, which follow, the preferred form of the composition is an aqueous solution.

EXAMPLE 5

| Component | % |
|---|---|
| Eflornithine monohydrate* | 15 |
| Poloxamer 185 | 10 |
| Water | 75 |

*Equivalent to 13.9% Eflornithine

The above composition was prepared by simple admixture of the components, with gentle heating, and, if need be, with stirring.

EXAMPLE 6

| Component | % |
|---|---|
| Eflornithine monohydrate* | 15 |
| Poloxamer 407 | 10 |
| Water | 75 |

*Equivalent to 13.9% Eflornithine

The above composition was prepared by the method outlined in Example 5.

EXAMPLE 7

| Component | % |
|---|---|
| Eflornithine monohydrate* | 15 |
| Steareth-20 | 5 |
| Steareth-100 | 5 |
| Water | 75 |

*Equivalent to 13.9% Eflornithine

The above composition was prepared in accordance with the method described in Example 5.

EXAMPLE 8

| Component | % |
|---|---|
| Eflornithine monohydrate* | 15 |
| N,N-dimethyldodecylamine N-oxide ("LDAO") | 0.5 |
| Water | 84.5 |

*Equivalent to 13.9% Eflornithine

The above composition was prepared in accordance with the method described in Example 5.

The compositions of Examples 2 through 8 were evaluated as described in Example 1. Follicular enhancement ratios were determined and graphically depicted in FIGS. 1 through 3.

Figure 1:
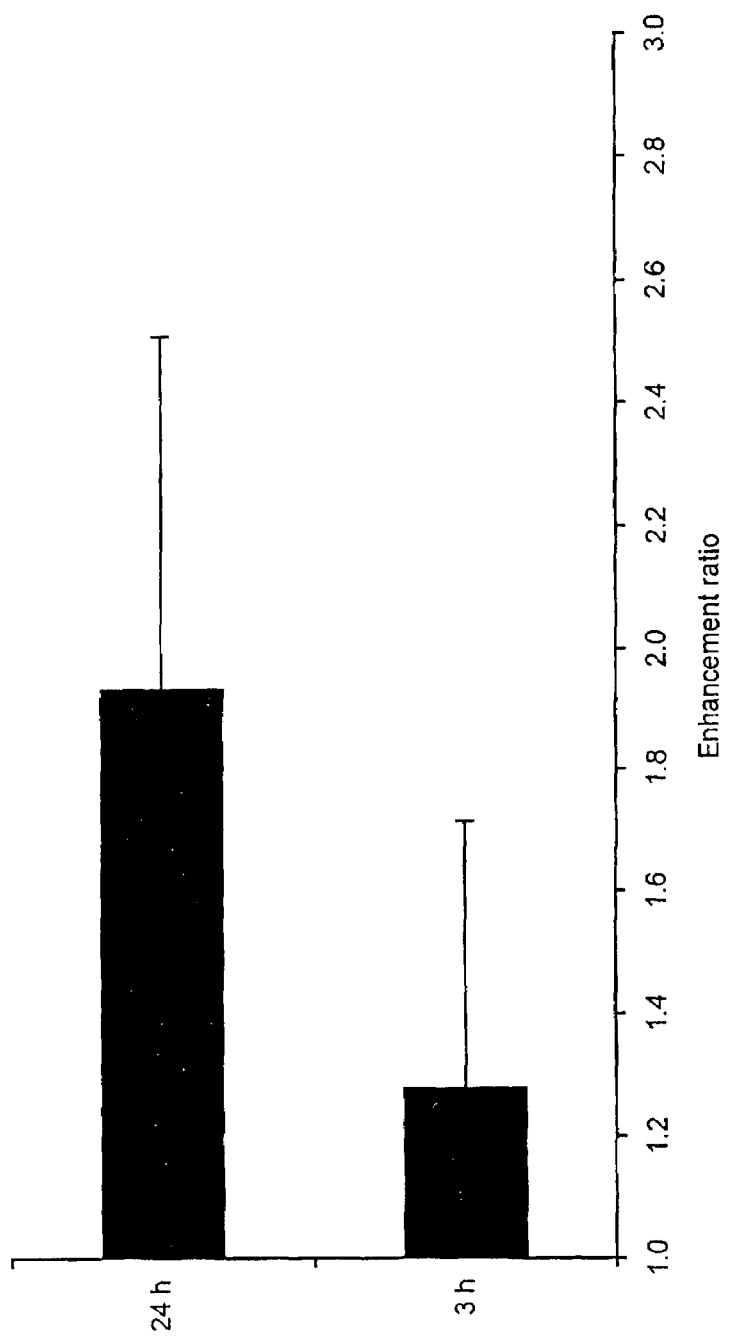
FIG. 1 shows that the delivery of Eflornithine to the hair follicles of cadaver beard skin for steareth-20/steareth-100 lotion A (Example 2) is about 1.3 and 2 fold compared to that of Vaniqa® at 3 and 24 hours following in vitro skin diffusion studies, respectively. This shows that the combination of steareth-20 and steareth-100 is capable of enhancing the delivery of Eflornithine to the hair follicle target site and maintaining its concentration in the hair follicle over a prolonged period of time.
Figure 2:
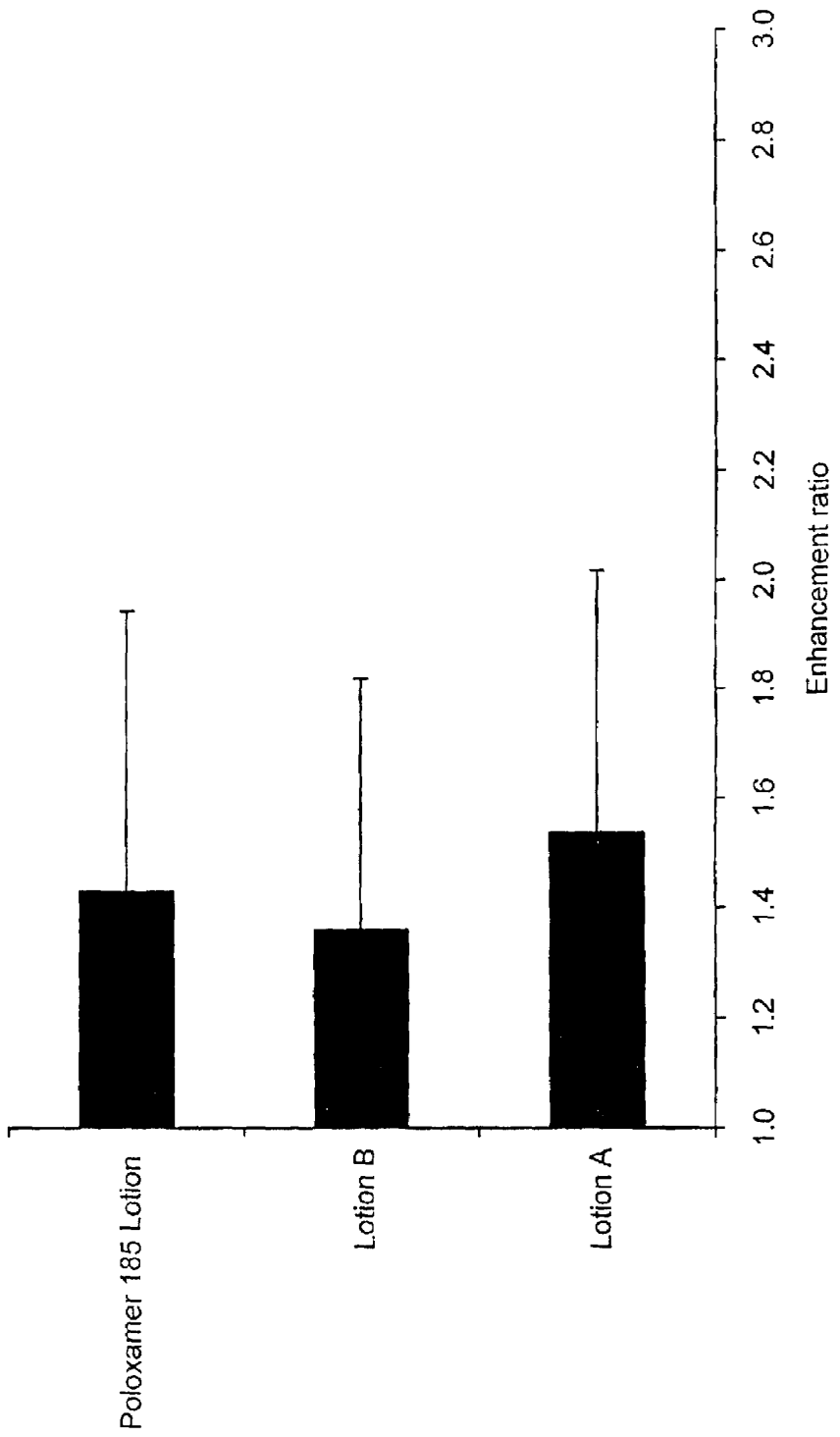
FIG. 2 shows that the delivery of Eflornithine to the hair follicles of cadaver scalp skin for poloxamer 185 lotion (Example 4), steareth-20/steareth-100 lotion A (Example 2), and stearath-20/steareth-100 lotion B (Example 3) is about 1.3 to 1.5 fold greater than that of Vaniqa® at 3 hours following in vitro skin diffusion studies. This shows that the enhancing agents of the present invention (employed in Examples 2-4) are capable of enhancing the delivery of Eflornithine to the hair follicle target site.
Figure 3:
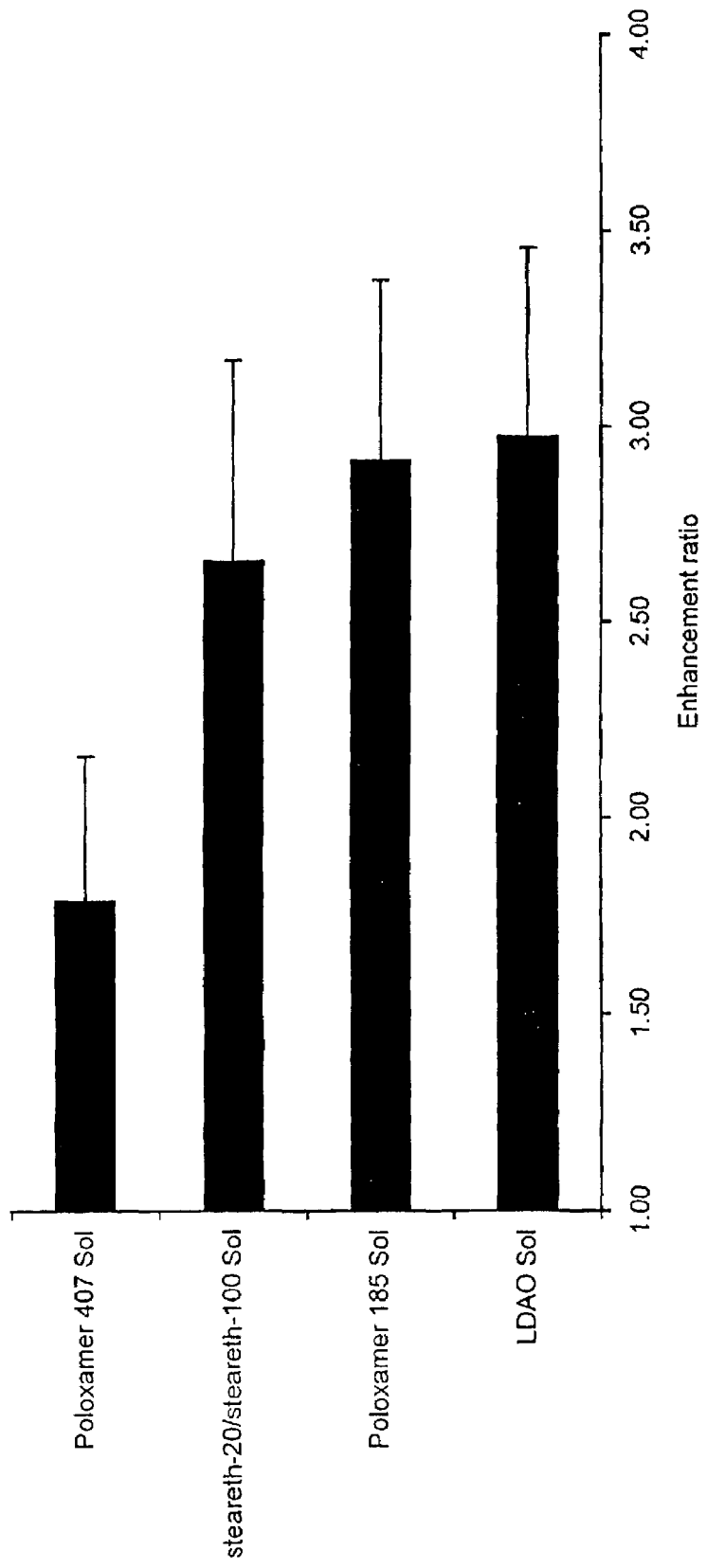
FIG. 3 shows that the delivery of Eflornithine to the hair follicles of cadaver scalp skin employing Eflornithine solutions containing one of the following enhancers: poloxamer 407 (Example 6), steareth-20/steareth-100 (Example 7), poloxamer 185 (Example 5), and N,N-dimethyl dodecylamine N-oxide ("LDAO") (Example 8) is increased 2 to 3 fold compared to Vaniqa® Cream.

To demonstrate that of the many penetration enhancers available to those skilled in the art only the enhancers of the present invention surprisingly increase follicular delivery of ODC inhibitors, particularly Eflornithine, and/or increase the duration of ODC inhibitors, particularly Eflornithine, in the hair follicle, the present inventors evaluated numerous skin penetration enhancers using the techniques described in the instant application. The skin penetration enhancers tested failed to enhance the follicular delivery of Eflornithine. They also failed to increase the residence time of Eflornithine in the hair follicle. In point of fact they actually had the opposite effect. In other words they had a negative effect on the follicular delivery and follicular residence time of Eflornithine. The skin penetration enhancers tested were:
  2% decyl methyl sulfate;
  10% isopropyl myristate+15% propylene glycol;
  20% diethylene glycol monoethyl ether (Transcutol®);
  5% polyoxyethylene-4-sorbitan monostearate (Tween® 61);
  0.5% dioctyl sodium sulfosuccinate;
  20% glycerin+0.5% LDAO; and
  0.38% polysorbate 20 (Tween®20)+0.12% polysorbate 61 (Tween® 61).

Many penetration enhancers known in the art can enhance the penetration of Eflornithine across the skin. However, of the numerous penetration enhancers tested, the present inventors surprisingly found that only the enhancers of the present invention target Eflornithine to the hair follicle and/or increase its residence time in the hair follicle. Skin penetration enhancers often couple enhanced penetration of a drug with the possibility of the drug being absorbed and causing systemic toxicity. The present invention enables targeting of ODC inhibitors, particularly Eflornithine, to the hair follicle thereby minimizing the possibility of systemic toxicity. Since not all skin penetration enhancers increase the delivery of ODC inhibitors, such as Eflornithine, and/or increase residence time of same in the hair follicle, there is evidently no correlation between skin penetration enhancement and follicular delivery enhancement. Clearly one skilled in the art could not have predicted that the enhancers of the instant invention would enhance the follicular delivery of ODC inhibitors, such as Eflornithine, and/or increase their residence time in the hair follicle.

The contents of all patents, patent applications, published articles, books, reference manuals and abstracts cited herein are hereby incorporated by reference in their entirety to more fully describe the state of the art to which the invention pertains.

As various changes can be made in the above-described subject matter without departing from the scope and spirit of the invention, it is intended that all subject matter contained in the above description, shown in the accompanying drawings, or defined in the appended claims, be interpreted as descriptive and illustrative, and not in a limiting sense. Many modifications and variations of the present invention are possible in light of the above teachings. It is therefore to be understood that within the scope of the appended claims, the invention may be practiced otherwise than as specifically described.

What is claimed is:

1. A topical composition for follicular delivery of an ornithine decarboxylase inhibitor to an area of mammalian skin containing hair follicles, the composition comprising:
   a) an amount of an ornithine decarboxylase inhibitor selected from the group consisting of 2-(difluoromethyl)-2,5-diaminopentanoic acid, alpha-ethynyl ornithine, 6heptyne-2,5-diamine,2-methyl-6-heptyne-2,5-diamine, and pharmaceutically acceptable salts, hydrates, optical enantiomers, and racemic mixtures thereof sufficient to deliver 1 to 2000 micrograms of the ornithine decarboxylase inhibitor per square centimeter ($cm^2$) of the skin;
   b) 1.0 to 25% of a follicular delivery enhancer, which provides a follicular enhancement ratio of at least 1.3 and is selected from the group consisting of poloxamer 185, poloxamer 407, N,N-dimethyl dodecylamine N-oxide, steareth-100, and mixtures thereof; and
   c) a pharmaceutically acceptable carrier.

2. The composition, as claimed in claim 1, wherein the inhibitor is 2-(difluoromethyl)-2,5-diaminopentanoic acid or a pharmaceutically acceptable salt, hydrate, (R) enantiomer, (S) enantiomer, or racemic mixture thereof.

3. The composition, as claimed in claim 1, wherein the inhibitor is 2-(di fluoromethyl)-2,5-diaminopentanoic acid.

4. The composition, as claimed in claim 1, wherein the ihhibitor is the R enantiomer of 2-(difluoromethyl)-2,5-diaminopentanoic acid.

5. The composition, as claimed in claim 1, wherein the composition is a water-in-oil emulsion, an oil-in-water emulsion, a solution, a gel, a cream, a stick, an ointments a paste, a shampoo, a foam, a patch or a mousse.

6. The composition, as claimed in claim 1, wherein the composition is an oil-in-water emulsion based lotion or cream.

7. The composition, as claimed in claim 1, wherein the carrier is water and the composition is a solution.

8. The composition, as claimed in claim 1, wherein the follicular delivery enhancer is present in an amount from 2.5% to 20% w/w based on the total weight of the composition.

9. The composition, as claimed in claim 1, wherein the follicular delivery enhanceris present in an amount from 4% to 15% w/w based on the total weight of the composition.

10. The composition, as claimed in claim 1, wherein the follicular delivery enhancer is present in an amount from 5% to 10% w/w based on the total weight of the composition.

11. The composition, as claimed in claim 1, wherein the follicular delivery enhancer is present in an amount of at least 3% w/w based on the total weight of the composition.

12. The composition, as claimed in claim 1, wherein the follicular delivery enhancer is present in an amount of at least4% w/w based on the total weight of the composition.

13. The composition, as claimed in claim 1, wherein the follicular delivery enhancer comprises steareth-100.

14. The composition, as claimed in claim 13, further comprising steareth-20.

15. The composition, as claimed in claim 1, wherein the follicular delivery enhancer comprises poloxamer 185.

16. The composition, as claimed in claim 1, wherein the follicular delivery enhancer comprises poloxamer 407.

17. The composition, as claimed in claim 1, wherein the follicular delivery enhancer comprises N,N-dimethyl dodecylamine-N-oxide.

18. The composition, as claimed in claim 1, further comprising an amount of an inhibitor of S-adenosyl methionine decarboxylase effective to reduce the rate and alter the character of mammalian hair growth.

19. The composition, as claimed in claim 18, wherein the inhibitor of S-adenosyl methionine decarboxylase is selected from the group consisting of methylglyoxal bis (guanylhydrazone), diethylglyoxal bis (guanylhydrazone), and 5'-deoxy-5'-{N-methyl-N-}aminoadenosine.

20. The composition, as claimed in claim 14, wherein 5% w/w steareth-20 and 5% w/w stearelh-100, based on the total weight of the composition, are present.

21. The composition, as claimed in claim 15, where in the poloxamer 185 is present in an amount of 10% w/w based on the total weight of the composition.

22. The composition, as claimed in claim 16, wherein poloxamer 407 is present in an amount of 10% w/w based on the total weight of the composition.

23. The composition, as claimed in claim 17, wherein N,N-dimethyl dodecylamine N-oxide is present in an amount of 0.5% w/w based on the total weight of the composition.

24. The composition, as claimed in claim 14, further comprising ceteareth-20.

25. The composition, as claimed in claim 24, wherein 5% w/w steareth-20, 5% w/w steareth-100, and 2.5% w/w cetearyl alcohol and ceteareth-20, based on the total weight of the composition, are present.

26. The composition, as claimed in claim 14, wherein the steareth-20 and steareth-100are present in a ratio of 1:1.

* * * * *